United States Patent
Stopek et al.

(10) Patent No.: US 10,098,633 B2
(45) Date of Patent: *Oct. 16, 2018

(54) BIOACTIVE SUBSTANCE IN A BARBED SUTURE

(71) Applicant: Covidien LP, Mansfield, MA (US)

(72) Inventors: Joshua B. Stopek, Minneapolis, MN (US); Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 302 days.

This patent is subject to a terminal disclaimer.

(21) Appl. No.: 15/061,037

(22) Filed: Mar. 4, 2016

(65) Prior Publication Data

US 2016/0183941 A1  Jun. 30, 2016

Related U.S. Application Data (63) Continuation of application No. 11/899,852, filed on Sep. 6, 2007, now Pat. No. 9,307,983.

(Continued)

(51) Int. Cl.
*A61B 17/04* (2006.01)
*A61B 17/06* (2006.01)
(Continued)

(52) U.S. Cl.
CPC .. *A61B 17/06166* (2013.01); *A61B 17/06066* (2013.01); *A61L 17/005* (2013.01); *A61B 2017/00004* (2013.01); *A61B 2017/00336* (2013.01); *A61B 2017/00884* (2013.01); *A61B 2017/00889* (2013.01); *A61B 2017/00893* (2013.01); *A61B 2017/06057* (2013.01); *A61B 2017/06176* (2013.01); *A61L 2300/404* (2013.01); *A61L 2300/406* (2013.01); *A61L 2300/41* (2013.01); *A61L 2300/416* (2013.01); *A61L 2300/418* (2013.01); *A61L 2300/602* (2013.01)

(58) Field of Classification Search
CPC .... A61B 17/06166; A61B 2017/06057; A61B 2017/06176; A61L 17/005; A61L 17/06
See application file for complete search history.

(56) References Cited

U.S. PATENT DOCUMENTS 3,942,532 A   3/1976 Hunter et al.
4,024,871 A   5/1977 Stephenson
(Continued)

FOREIGN PATENT DOCUMENTS

EP   0326426 A2   8/1989
EP   0499048 A1   8/1992
(Continued)

OTHER PUBLICATIONS

European Examination Report from Appl. No. 10 177 651.6 dated Sep. 19, 2016.
(Continued)

*Primary Examiner* — Gregory Anderson (57) ABSTRACT

Barbed surgical sutures are prepared with a bioactive agent thereon. In embodiments, the bioactive agent may be an antimicrobial or clotting agent deposited within the angle formed by the barb and the suture body. Placement of the bioactive agent in the angle between the barb and suture body enhances the delivery of the bioactive agent to wound tissue at the point of contact.

24 Claims, 4 Drawing Sheets

Related U.S. Application Data (60) Provisional application No. 60/842,763, filed on Sep. 6, 2006.

(51) Int. Cl.
*A61L 17/00* (2006.01)
*A61B 17/00* (2006.01)

(56) References Cited

U.S. PATENT DOCUMENTS

| | | | |
|---|---|---|---|
| 4,185,637 | A | 1/1980 | Mattei |
| 5,089,013 | A | 2/1992 | Bezwada et al. |
| 5,123,913 | A | 6/1992 | Wilk et al. |
| 5,133,738 | A | 7/1992 | Korthoff et al. |
| 5,226,912 | A | 7/1993 | Kaplan et al. |
| 5,236,563 | A | 8/1993 | Loh |
| 5,342,376 | A | 8/1994 | Ruff |
| 5,569,302 | A | 10/1996 | Proto et al. |
| 5,814,056 | A | 9/1998 | Prosst et al. |
| 5,931,855 | A | 8/1999 | Buncke |
| 6,063,105 | A | 5/2000 | Totakura |
| 6,106,505 | A | 8/2000 | Modak et al. |
| 6,143,352 | A | 11/2000 | Clark et al. |
| 6,165,202 | A | 12/2000 | Kokish et al. |
| 6,203,564 | B1 | 3/2001 | Hutton et al. |
| 6,235,869 | B1 | 5/2001 | Roby et al. |
| 6,241,747 | B1 | 6/2001 | Ruff |
| 6,270,517 | B1 | 8/2001 | Brotz |
| 6,506,197 | B1 | 1/2003 | Rollero et al. |
| 6,514,271 | B2 | 2/2003 | Evans et al. |
| 6,562,051 | B1 | 5/2003 | Bolduc et al. |
| 6,599,310 | B2 | 7/2003 | Leung et al. |
| 6,620,846 | B1 | 9/2003 | Jonn et al. |
| 6,773,450 | B2 | 8/2004 | Leung et al. |
| 9,307,983 | B2 | 4/2016 | Stopek et al. |
| 2002/0077661 | A1 | 6/2002 | Saadat |
| 2002/0177876 | A1 | 11/2002 | Roby et al. |
| 2003/0074023 | A1 | 4/2003 | Kaplan et al. |
| 2003/0149447 | A1 | 8/2003 | Morency et al. |
| 2004/0010275 | A1 | 1/2004 | Jacobs et al. |
| 2004/0030354 | A1 | 2/2004 | Leung et al. |
| 2004/0060409 | A1 | 4/2004 | Leung et al. |
| 2004/0060410 | A1 | 4/2004 | Leung et al. |
| 2004/0088003 | A1 | 5/2004 | Leung et al. |
| 2004/0153125 | A1 | 8/2004 | Roby |
| 2004/0162580 | A1 | 8/2004 | Hain |
| 2005/0033367 | A1 | 2/2005 | Leung et al. |
| 2005/0267531 | A1 | 12/2005 | Ruff et al. |
| 2006/0111734 | A1 | 5/2006 | Kaplan et al. |
| 2006/0116718 | A1 | 6/2006 | Leiboff |
| 2007/0005110 | A1 | 1/2007 | Collier et al. |
| 2007/0187861 | A1 | 8/2007 | Genova et al. |
| 2007/0224237 | A1 | 9/2007 | Hwang et al. |
| 2009/0210006 | A1 | 8/2009 | Cohen et al. |
| 2010/0016891 | A1 | 1/2010 | Kennedy et al. |

FOREIGN PATENT DOCUMENTS

| | | | |
|---|---|---|---|
| EP | 0632999 | A1 | 1/1995 |
| EP | 0647452 | A1 | 4/1995 |
| EP | 1062278 | B1 | 5/2006 |
| EP | 1669093 | A1 | 6/2006 |
| EP | 1897500 | A1 | 3/2008 |
| EP | 1955720 | A1 | 8/2008 |
| WO | 9708238 | A1 | 3/1997 |
| WO | 9800065 | A1 | 1/1998 |
| WO | 9852473 | A1 | 11/1998 |
| WO | 9942528 | A2 | 8/1999 |
| WO | 9952451 | A1 | 10/1999 |
| WO | 0057933 | A1 | 10/2000 |
| WO | 0152751 | A1 | 7/2001 |
| WO | 03001979 | A2 | 1/2003 |
| WO | 03088818 | A2 | 10/2003 |
| WO | 03088846 | A1 | 10/2003 |
| WO | 2004014236 | A1 | 2/2004 |
| WO | 2004030520 | A2 | 4/2004 |
| WO | 2004030704 | A2 | 4/2004 |
| WO | 2004030705 | A2 | 4/2004 |
| WO | 2004045663 | A1 | 6/2004 |
| WO | 2004066927 | A2 | 8/2004 |
| WO | 2005080495 | A1 | 9/2005 |
| WO | 2006079469 | A1 | 8/2006 |
| WO | 2007133103 | A1 | 11/2007 |
| WO | 2008042909 | A2 | 4/2008 |
| WO | 2008107919 | A1 | 9/2008 |
| WO | 2008141034 | A1 | 11/2008 |
| WO | 2009/132284 | A2 | 10/2009 |

OTHER PUBLICATIONS

JLT1204-211-229 (175): R. R. Szarmach et al., Journal of Long-Term Effects of Medical Implants, "An Innovative Surgical Suture and Needle Evaluation andSelection Program" 12(4), pp. 211-229 (2002).

George Odian, "Principles of Polymerization", III Edition, pp. 569-573 (1991).

International Search Report from Appln. No. EP 06 012688 dated Aug. 1, 2007.

Partial European Search Report dated Jan. 22, 2008.

European Search Report (EP 07 25 3438 dated Feb. 1, 2008).

European Search Report from application No. 07 25 4703 dated Feb. 10, 2009.

European Search Report from application No. 07 25 4341 dated Apr. 20, 2009.

European Search Report for Appln. No. 09251035.3 dated Jun. 3, 2009.

European Search Report for Appln. No. 09250460 dated Jun. 2, 2009.

European Search Report for EP 09007757.9-1526 date of completion is Aug. 10, 2009 (3 pages).

European Search Report for EP 10177651.6-1526 date of completion is Dec. 10, 2010 (3 pages).

European Search Report for Application No. EP 08 25 3618 dated Jul. 25, 2011.

European Search Report corresponding to European Application No. EP11 25 0289.3-1455 / 2380599, dated Oct. 23, 2013; 9 pages.

Lendlein A et al: "Shape-Memory Polymers as Stimuli-Sensitive Implant Materials", Clinical Hemorheology and Microcirculation, IOS Press, Amsterdam, NL, vol. 32, No. 2, 2005, pp. 105-116.

Lendlein A et al: "Shape-memory polymers", Angewandte Chemie. International Edition, Wiley VCH Verlag, Weinheim, vol. 41, No. 12, Jun. 17, 2002, pp. 2034-2057.

"Solving a Knotty Problem—Surgical Sutures From Shape Memory Polymers", Materials World, The Institute of Materials, London, GB, vol. 10, No. 7, Jul. 2002, pp. 29/30.

Elisa Zini et al.: "Shape Memory Behavior of Novel (L-Lactide-Glycolide-trimethylene Carbonate) Terpolymers", Biomacromolecules, vol. 8, 2007, pp. 3661-3667.

BIOACTIVE SUBSTANCE IN A BARBED SUTURE

CROSS-REFERENCE TO RELATED APPLICATIONS

This application is a continuation of U.S. patent application Ser. No. 11/899,852 filed Sep. 6, 2007, which claims benefit of and priority to U.S. Provisional Application No. 60/842,763 filed Sep. 6, 2006, and the disclosures of each of the above-identified applications are hereby incorporated by reference in their entirety.

TECHNICAL FIELD

This application claims the benefit of U.S. Provisional Patent Application No. 60/842,763 filed Sep. 6, 2006, the entire disclosure of which is hereby incorporated by reference herein.

BACKGROUND OF RELATED ART

Barbed sutures, which are generally made of the same materials as conventional sutures, offer several advantages for closing wounds compared with conventional sutures. A barbed suture includes an elongated body that has one or more spaced barbs, which project from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in cosmetic, laparoscopic and endoscopic procedures. Using barbed sutures enables the placement of tension in tissue with less slippage of the suture in the wound. The number of suture barbs may be influenced by the size of the wound and the strength required to hold the wound closed. Like a conventional suture, a barbed suture may be inserted into tissue using a surgical needle.

Bioactive agents such as antimicrobial agents have been associated with surgical devices such as to prevent microbial infections during the wound healing process. It is also known to coat surgical sutures with antimicrobial compounds to prevent and treat microbial infections.

While antimicrobial agents have been used for surgical sutures and wound dressings to prevent infections, a continuing need exists for improved barbed sutures that can remain in vivo for extended periods of time with enhanced antimicrobial efficacy. There is also a need for easy and inexpensive methods of improving the antimicrobial characteristics of barbed sutures for extended periods of time thus permitting the use of lower amounts of antimicrobial agents to achieve the desired antimicrobial effect in vivo. There is also a need for delivery of other bioactive agents to wound sites to promote healing and the like.

SUMMARY

A surgical suture is provided having an elongated body comprising at least one filament having a proximal end and a distal end. The suture includes barbs projecting from the elongated body towards at least one end thereby forming an included angle of less than about 90 degrees between the barbs and the suture body. In embodiments, a bioactive agent may be deposited within the barb angles, that is, the angle formed between the barb and suture surface.

In yet a further embodiment, a method for repairing tissue with the sutures of the present disclosure is also provided.

BRIEF DESCRIPTION OF THE DRAWINGS

Various embodiments of the present disclosure will be described herein below with reference to the figures wherein.

DETAILED DESCRIPTION

Described herein are barbed surgical sutures. Sutures in accordance with the present disclosure may be of monofilament or multifilament construction. The suture may have both a proximal and distal end, with barbs projecting from the elongated body towards at least one end thereby forming an included angle of less than about 90 degrees between the barbs and the suture body. In embodiments, a bioactive agent may be deposited within the barb angles, that is, the angle formed between the barb and suture surface. Placement of a bioactive agent in the angle formed between the barbs and suture surface places the bioactive agent at precisely defined locations within a tissue wound closure, which thereby provides a unique controlled and sustained release dosage form.

Barbed sutures in accordance with the present disclosure may be formed of degradable materials, non-degradable materials, and combinations thereof. Suitable degradable materials which may be utilized to form the medical device include natural collagenous materials or synthetic resins including those derived from alkylene carbonates such as trimethylene carbonate, tetramethylene carbonate, and the like, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates (PHB), polyorthoester, polyhydroxy alkanoates, homopolymers thereof, copolymers thereof, and combinations thereof. In some embodiments, glycolide and lactide based polyesters, especially copolymers of glycolide and lactide may be utilized to form a suture of the present disclosure.

Suitable non-degradable materials which may be utilized to form the sutures of the present disclosure include polyolefins, such as polyethylene, polypropylene, copolymers of polyethylene and polypropylene, and blends of polyethylene and polypropylene; ultra high molecular weight polyethylene, polyamides (also known as nylon); polyesters such as polyethylene terephthalate; polytetrafluoroethylene; polyether-esters such as polybutester; polytetramethylene ether glycol; 1,4-butanediol; polyurethanes; and combinations thereof. In other embodiments, non-degradable materials may include silk, cat gut, cotton, linen, carbon fibers, and the like. In some useful embodiments, polypropylene can be utilized to form the suture. The polypropylene can be isotactic polypropylene or a mixture of isotactic and syndiotactic or atactic polypropylene.

Filaments used for forming sutures of the present disclosure may be formed using any technique within the purview of those skilled in the art, such as, for example, extrusion, molding and/or solvent casting.

In embodiments, the suture of the present disclosure may include a yarn made of more than one filament, which may contain multiple filaments of the same or different materials. Where the sutures are made of multiple filaments, the suture can be made using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process. In one embodiment a multifilament suture of the present disclosure can be produced by braiding. The braiding can be done by any method within the purview of those skilled in the art.

Once the suture is constructed, it can be sterilized by any means within the purview of those skilled in the art.

Sutures in accordance with the present disclosure may be coated or impregnated with one or more medico-surgically useful substances, e.g., bioactive agents which accelerate or beneficially modify the healing process when the suture is applied to a wound or surgical site. Suitable bioactive agents include, for example, biocidal agents, antimicrobial agents, medicants, growth factors, anti-clotting agents, clotting agents, analgesics, anesthetics, anti-inflammatory agents, wound repair agents and the like, chemotherapeutics, biologics, protein therapeutics, antibodies, DNA, RNA, peptides, polysaccharides, lectins, lipids, anti-angiogenic drugs, polymeric drugs, and combinations thereof.

Bioactive agents include substances which are beneficial to the animal and tend to promote the healing process. For example, a suture can be provided with a bioactive agent that may be deposited at the sutured site. The bioactive agent can be chosen for its antimicrobial properties, capability for promoting wound repair and/or tissue growth, or for specific indications such as thrombosis. In embodiments, combinations of such agents may be applied to a suture of the present disclosure.

The term "antimicrobial agent" as used herein includes an agent which helps the body destroy or resist pathogenic (disease-causing) microorganisms. An antimicrobial agent includes antibiotics, antiseptics, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other with other bioactive agents described herein: an anthracycline, doxorubicin, mitoxantrone, a fluoropyrimidine, 5-fluorouracil (5-FU), a folic acid antagonist, methotrexate, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Synercid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of antiseptics and disinfectants which may be utilized as the antimicrobial agent include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some useful embodiments, at least one of the antimicrobial agents may be an antiseptic such as triclosan.

To promote wound repair and/or tissue growth, one or more bioactive agents known to achieve either or both of these objectives can also be applied to the suture as wound repair agents or tissue growth agents. Such clotting or "fibrosis-inducing agents" are utilized for the promotion of aneurysm or embolism when it is desired for treatment of particular vascular insults or diseases, or for example, blocking a tumor from its primary blood supply. In embodiments, the barbed suture having a clotting agent deposited within the barb angles in accordance with the present disclosure may contribute to platelet and blood component capture.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, polylysine, fibronectin, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethyistibesterol, cyclosporine a, all-trans retinoic acid or an analogue or derivative thereof, wool (including animal wool, wood wool, and mineral wool), cotton, bFGF, polyurethane, polytetrafluoroethylene, poly(alkylcyanoacrylate), activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, an inhibitor of matrix metalloproteinase, magainin, tissue or kidney plasminogen activator, a tissue inhibitor of matrix metalloproteinase, methotrexate, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, α,α-dipyridyl, β-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Sutures in accordance with this disclosure can also include, for example, biologically acceptable plasticizers, antioxidants and colorants, which can be impregnated into the filament(s) utilized to form a suture of the present disclosure or included in a coating thereon.

As noted above, bioactive agents may be impregnated into the materials utilized to form sutures of the present disclosure or deposited on the surface thereof. Bioactive agents may be applied onto a barbed suture of the present disclosure utilizing any method within the purview of one skilled in the art including, for example, dipping, spraying, vapor deposition, brushing, compounding and the like.

In embodiments the bioactive agent, such as an antimicrobial agent, may be applied to a barbed suture of the present disclosure as part of a bioactive agent solution. The bioactive agent solution can include any solvent or combination of solvents suitable for the chosen bioactive agent. To be suitable, the solvent should (1) be miscible with the bioactive agent, and (2) not appreciably affect the integrity of any material used to form a medical device, such as the barbed suture. In some useful embodiments, the solvent utilized is a polar solvent. Some examples of suitable solvents include methylene chloride, chloroform, ethyl acetate, methyl acetate, N-methyl 2-pyrrolidone, 2-pyrrolidone, propylene glycol, tetrahydrofuran (THF), acetone, oleic acid, methyl ethyl ketone, water, and mixtures thereof. In one embodiment, methylene chloride may be used as a solvent.

The method of preparing the bioactive agent solution can be a relatively simple procedure including mixing, blending, and the like. Any known technique may be employed for applying the bioactive agent solution to the medical device. Suitable techniques include dipping, spraying, wiping, brushing, and the like.

The bioactive agent solution generally contains from about 0.1% to about 20% of the bioactive agent by weight, in embodiments from about 0.5% to about 5% of the bioactive agent by weight. The exact amount of the bioactive agent will depend on a number of factors, such as the particular agent used, the medical device being contacted and the choice of solvent employed. In one embodiment, where the bioactive agent is an antimicrobial agent, the antimicrobial solution may contain from about 0.1% to about 10% of the chosen antimicrobial agent, in embodiments from about 1% to about 5% of the antimicrobial agent.

The amount of the bioactive agent solution applied should be an effective amount to provide the desired bioactive properties to the suture. The exact amount will depend upon the configuration of the suture and the formulation of the solution. Since the bioactive agent solution contains a solvent, a curing step may be employed in useful embodiments to remove the solvent, leaving the bioactive agent on the suture. Suitable curing steps for removal of the solvent include, but are not limited to, evaporation and/or lyophilization. Upon removal of the solvent, the bioactive agent remains bound to the suture in the angle formed between the barb and suture body.

Regardless of the method of application, the amount of the bioactive agent on the suture can be from about 0.01% by weight of the suture to about 2% by weight of the suture, in embodiments from about 0.02% by weight of the suture to about 1% by weight of the suture, typically from about 0.05% by weight of the suture to about 0.5% by weight of the suture.

Once applied, the bioactive agent will not be lost due to evaporation, sublimation, volatilization, etc. during the subsequent handling, processing and storage of the barbed suture. However, upon application of the barbed suture in vivo, that is, after use in suturing a wound, the attachment of the barbs to the tissue will release the bioactive agent into the tissue.

In other embodiments, the bioactive agent may be included in a coating applied to the suture. Suitable coatings which may be utilized are within the purview of one skilled in the art and include, for example, biodegradable coatings such as those disclosed in U.S. Patent Publication No. 20040153125, the entire disclosure of which is incorporated by reference herein. Biodegradable polymers may be especially suitable as they will release the bioactive agent in vivo as the biodegradable polymer is resorbed by the body.

In embodiments, mixtures useful in forming the aforementioned coatings include a bioactive agent such as an antimicrobial agent as a predominant component in an effective antimicrobial amount. A "predominant amount" refers to one or more components which are present in an amount greater than about 50 weight percent. A "minor amount" refers to one or more components which are present in an amount up to about 50 weight percent. The minor component may include copolymers containing biodegradable monomers such as caprolactone.

An "effective antimicrobial amount" of a given component is an amount at which the component hinders the growth of bacteria to diminish or avoid contamination of the wound site.

In embodiments, the antimicrobial degradable coating composition for biocompatible surgical implantable devices is inexpensive, biocompatible, and not subject to excessive diffusion. "Biocompatible" means that no serious systemic toxicity is caused by the presence of an object in a living system. It is contemplated that biocompatible objects may cause some clinically acceptable amounts of toxicity including irritation and/or other adverse reactions in certain individuals.

Any biodegradable polymer within the purview of those skilled in the art can be employed in the present coatings. In embodiments, the biodegradable polymer may contain epsilon-caprolactone as a component thereof. Suitable caprolactone containing copolymers include copolymers which may be synthesized by well known conventional polymerization techniques. In some embodiments, suitable caprolactone containing copolymers are "star" copolymers obtained by polymerizing a predominant amount of epsilon-caprolactone and a minor amount of another biodegradable monomer polymerizable therewith in the presence of a polyhydric alcohol initiator.

In embodiments, the caprolactone containing copolymer may be obtained by polymerizing a predominant amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

In certain embodiments, the copolymer herein can contain from about 70 to about 98, and preferably from about 80 to about 95, weight percent epsilon-caprolactone derived units, the balance of the copolymer being derived from the other copolymerizable monomer(s).

Suitable monomers which can be copolymerized with epsilon-caprolactone include alkylene carbonates such as trimethylene carbonate, tetramethylene carbonate, dimethyl trimethylene carbonate; dioxanones; dioxepanones; degradable cyclic amides; degradable cyclic ether-esters derived from crown ethers; hydroxyacids capable of esterification, including both alpha hydroxyacids (such as glycolic acid and lactic acid) and beta hydroxyacids (such as beta hydroxybutyric acid and gamma hydroxyvaleric acid); polyalkyl ethers (such as polyethylene glycol and polypropylene glycol and combinations thereof); polyvinyl pyrrolidone, hydroxyethylmethacrylate, phosphorylcholine, acrylic acid, methacrylic acid, vinyl monomers, vinyl alcohols, vinyl acetate, and combinations thereof. In embodiments, a suitable monomer for use with the present disclosure is glycolide.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in relatively small amounts, e.g., from about 0.01 to about 5, and preferably from about 0.1 to about 3, weight percent of the total monomer mixture.

The coating composition can contain from about 0.3 to about 10, and preferably from about 0.5 to about 5, weight percent of the copolymer. Such a coating provides sutures with the combined desirable properties of improved handling characteristics and antimicrobial activity.

In addition to the antimicrobial agents described above, in some embodiments the coating may include one or more fatty acid components such as fatty acids, fatty acid salts and salts of fatty acid esters which may impart antimicrobial characteristics to the suture.

Where the coating includes a fatty acid metal salt, the fatty acid metal salt used as the antimicrobial agent may include metal stearates. In one embodiment, the fatty acid salt used as the antimicrobial agent is silver stearate. In another embodiment, the fatty acid salt(s) used as the antimicrobial agent may be combined with fatty acid esters such as stearoyl lactylates, particularly calcium stearoyl lactylate.

Suitable fatty acids which can be used in the present coatings include the biocompatible monovalent and polyvalent metal salts of fatty acids having 6 or more carbon atoms. Examples of fatty acids useful for forming a metal salt of a fatty acid useful herein includes butyric, caproic, caprylic, capric, lauric, myristic, palmitic, palmitoleic, stearic, oleic, linoleic, linolenic, etc. Examples of monovalent metals useful for forming a metal salt of a fatty acid useful in the various embodiments described herein include lithium, rubidium, cesium, francium, copper, silver and gold. Examples of polyvalent metals useful for forming a metal salt of a fatty acid useful in the various embodiments described herein include aluminum, tin, lead, bismuth and the polyvalent transition metals. Therefore, suitable metal salts of fatty acids useful herein include fatty acid salts of lithium, rubidium, cesium, francium, copper, silver, gold, beryllium, magnesium, strontium, barium, radium, aluminum, tin, lead, bismuth, zinc, cadmium, mercury, etc.

The metal salt of a fatty acid is present in the coating composition in an effective antimicrobial amount as defined above. The metal salt of a fatty acid can consist of a single chemical compound. However, the metal salt of a fatty acid can also be a mixture of several metal salts of fatty acids. The metal salt of a fatty acid may be present in an amount from about 30 percent to about 70 percent by weight of the coating composition, in embodiments from about 45 percent to about 55 percent by weight of the coating composition.

The metal salt of a fatty acid may be relatively insoluble in cold water. When desirable, a solvent may be used to improve the working properties, e.g., viscosity, miscibility, etc., of the metal salt of a fatty acid. Suitable solvents include, for example, alcohols, e.g., methanol, ethanol, propanol, chlorinated hydrocarbons (such as methylene chloride, chloroform, 1,2-dichloro-ethane), aliphatic hydrocarbons such as hexane, heptene, ethyl acetate). When desirable, heat may be applied to the solvent mixture of metal salts of fatty acids to improve their solubility. For example, temperatures ranging from about 30° C. to about 60° C. are appropriate.

In certain embodiments, fatty acid esters may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate; calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the tradename VERV from American Ingredients Co., Kansas City, Mo.) being preferred. When desirable, the fatty acid ester may be combined with a solvent. Suitable solvents include those listed above.

Where the bioactive agent is included as part of a coating, the bioactive agent and coating components may be added to separate solvents, and the resulting solvent mixtures may then be combined to form a coating solution. In other embodiments, the bioactive agent and coating components may be combined together and then mixed with solvent to form a coating solution or any combination. The order of addition is not critical and therefore may be determined through routine experimentation depending upon the desired use.

The coating can be applied to a suture by any suitable process, e.g., passing the suture through a solution of the coating mixture, past a brush or other coating solution applicator, or past one or more spray nozzles dispensing the suture coating solution. The coating solution can contain from about 30 to about 70, in embodiments from about 45 to about 55, weight percent solvent. In embodiments, a mixture of methylene chloride, hexane and ethanol may be used as a solvent. The suture wetted with the coating solution may be optionally passed through or held in a drying oven for a time and at a temperature sufficient to vaporize and drive off the solvent. If desired, the suture coating composition can optionally contain additional bioactive agents or components described above, e.g., dyes, antibiotics, antiseptics, growth factors, anti-inflammatory agents, etc.

Barbs may be formed on the surface of the body of a suture utilizing any method within the purview of one skilled in the art. Such methods include, but are not limited to, cutting, molding, and the like. In some embodiments, barbs may be formed by making with acute angular cuts directly into the suture body, with cut portions pushed outwardly and separated from the body of the suture. The depth of the barbs thus formed in the suture body may depend on the diameter of the suture material and the depth of the cut. In some embodiments, a suitable device for cutting a plurality of axially spaced barbs on the exterior of a suture filament may use a cutting bed, a cutting bed vise, a cutting template, and a blade assembly to perform the cutting. In operation, the cutting device has the ability to produce a plurality of axially spaced barbs in the same or random configuration and at different angles in relation to each other. Other suitable methods of cutting the barbs include the use of a laser or manual methods. The suture could also be formed by injection molding, extrusion, stamping and the like. The suture can be packaged in any number of desired pre-cut lengths and in pre-shaped curves.

In embodiments, all of the barbs may be aligned to allow the suture to move through tissue in one direction and resist moving through tissue in the opposite direction. For example, referring to FIG. 1, the barbs 12 on a suture 10 may be formed into a single directional suture. In embodiments suture 10 may be attached to needle 16. The barbs 12 are yieldable toward the body 14 of suture 10. The barbs 12 permit movement of suture 10 through tissue in the direction of movement of a needle end 16 but are generally rigid in an opposite direction and prevent movement of suture 10 in a direction opposite the direction of movement of a needle end 16.

Figure 1:
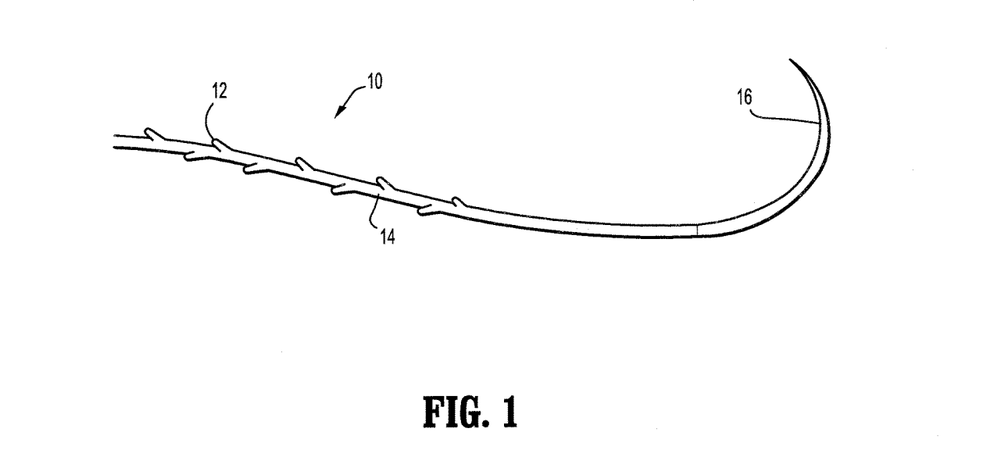
FIG. 1 is a perspective view of a barbed suture in accordance with the present disclosure attached to a needle.

Suture 10 may include a bioactive agent (not shown) disposed within the angle between the barb 12 and suture body 14.

Alternatively, a multifilament suture (not shown) may be utilized which may include filaments fabricated from biocompatible degradable polymers, biocompatible non-degradable polymers, or combinations thereof. In embodiments, a multifilament suture may be provided which includes a biocompatible degradable polymer which includes a bioactive agent disposed within the angle between the barb and suture body. In another embodiment, a multifilament suture may include individual filaments fabricated from a combination of biocompatible degradable polymer or biocompatible non-degradable polymer which includes a bioactive agent disposed within the angle between the barb and suture body.

Figure 2:
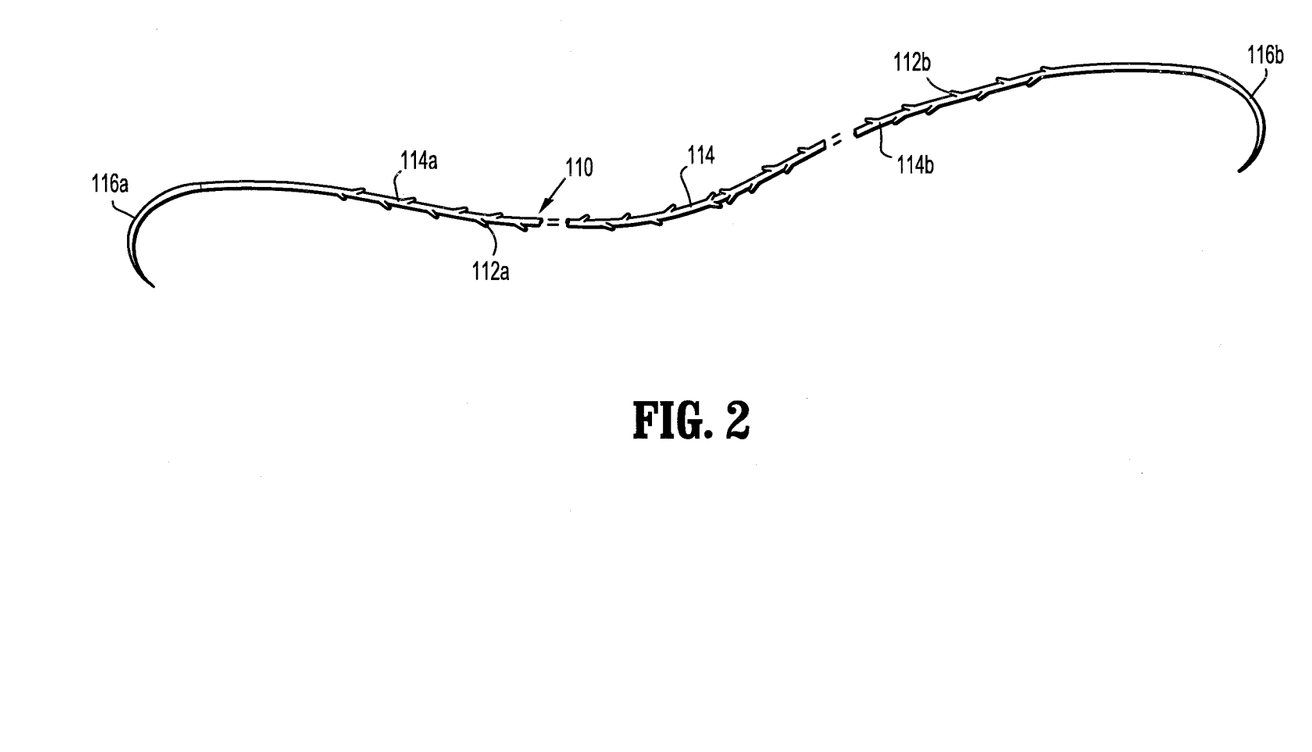
FIG. 2 is a perspective view of a bi-directional barbed suture attached to a needle on each end.

In other embodiments, the barbs may be aligned on a first portion of a length of a suture to allow movement of a first end of the suture through tissue in one direction, while barbs on a second portion of the length of the suture may be aligned to allow movement of the second end of the suture in an opposite direction. For example, as depicted in FIG. 2, a suture 110 may be bi-directional. Barbed suture 110 includes an elongated body 114 having two areas, body portion 114a and body portion 114b, distal first and second needle ends 116a and 116b for penetrating tissue, and a plurality of barbs 112a and 112b extending from the periphery of the body 114. An antimicrobial agent may be disposed within the angle formed between the barbs 112a and 112b and suture body 114. Barbs 112a on a first portion of the body 114a between the first end of suture 110 and a first axial location on the suture body permit movement of suture 110 through the tissue in a direction of movement of first needle end 116a and prevent movement of suture 110 relative to the tissue in a direction opposite the direction of movement of the first needle end 116a. Barbs 112b on second portion of body 114b between a second needle end 116b of a suture 114 and a second axial location on the body which is less than the distance from the second needle end 116b to the first axial location permit movement of a suture 114 through the tissue in a direction of movement of a second needle end 116b and prevent movement of a suture 114 relative to the tissue in a direction opposite the direction of movement of the second needle end 116b.

The barbs can be arranged in any suitable pattern, for example, in a helical pattern. The number, configuration, spacing and surface area of the barbs can vary depending upon the tissue in which the suture is used, as well as the composition and geometry of the material utilized to form the suture. Additionally, the proportions of the barbs may remain relatively constant while the overall length of the barbs and the spacing of the barbs may be determined by the tissue being connected. For example, if the suture is to be used to connect the edges of a wound in skin or tendon, the barbs may be made relatively short and more rigid to facilitate entry into this rather firm tissue. Alternatively, if the suture is intended for use in fatty tissue, which is relatively soft, the barbs may be made longer and spaced further apart to increase the ability of the suture to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In embodiments a single directional suture as depicted in FIG. 1 may have both large and small barbs; in other embodiments a bi-directional suture as depicted in FIG. 2 may have both large and small barbs.

In embodiments, sutures of the present disclosure may be dyed in order to increase the visibility of the suture in the surgical field. Any dye suitable for incorporation in sutures can be used. Such dyes include, but are not limited to, carbon black, bone black, D&C Green No. 6, and D&C Violet No. 2. In embodiments, sutures in accordance with the present disclosure may be dyed by adding dye in an amount up to about a few percent, in other embodiments by adding dye in an amount of about 0.2%, in still further embodiments in an amount from about 0.06% to about 0.08%.

In order to facilitate needle attachment to a suture of the present disclosure, conventional tipping agents can be applied to the braid. Two tipped ends of the suture may be desirable for attaching a needle to each end of the suture to provide a so-called double armed suture. The needle attachment can be made by any conventional method such as crimping, swaging, etc, as is known within the purview of those skilled in the art. Wounds may be sutured by passing the needled suture through tissue to create wound closure. The coating, in addition to enhancing the suture's handling characteristics, advantageously possesses antimicrobial properties to promote healing and prevent infection.

Figure 3A:
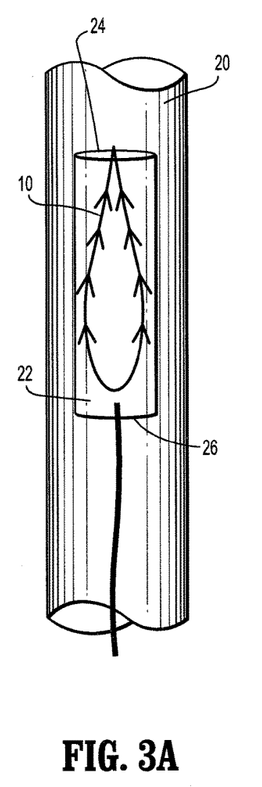
FIGS. 3A-3C are plan views of a tubular insertion device utilized with a barbed suture in accordance with the present disclosure.
Figure 3B:
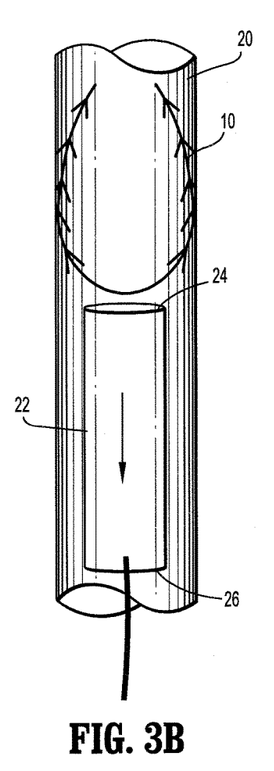
Figure 3C:
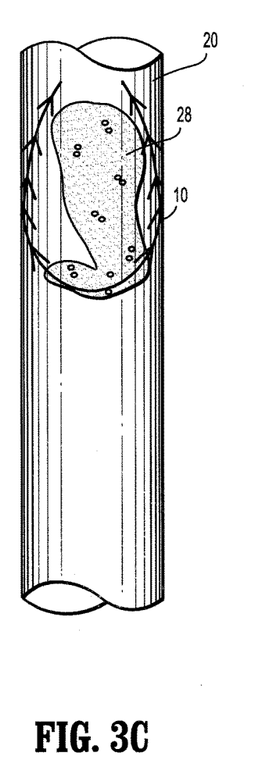

In some embodiments, the barb contribution to the architecture of the suture or a wound closure device may contribute to platelet and blood component capture. Referring to FIGS. 3A, 3B, 3C, a tubular insertion device 22 may be utilized to introduce a barbed suture 10 in accordance with the present disclosure into a blood vessel 20. Such a tubular insertion device 22 may have a tubular body in which the barbed suture 10 is disposed, as well as a distal end 24 and a proximal end 26. In use, the pointed end of a barbed suture 10 of the present disclosure may be pushed with the distal end 24 of the tubular insertion device through skin, tissue, vessels, and the like at an insertion point. The pointed end of barbed suture 10 and the distal end 24 of the tubular insertion device are pushed through the tissue until reaching an endpoint. The proximal end 26 of the tubular insertion device 22 is then gripped and pulled to remove the insertion device 22, leaving the barbed suture 10 in place.

For ease of movement of the tubular insertion device, the tubular insertion device 22 may include a string, wire, or the like to pull and remove the insertion device 22 from the barbed suture as illustrated in FIG. 3B. In exemplary embodiments, the tubular insertion device 22 is deployed from barbed suture 10, which allows for barbed suture 10 to expand to full vessel thickness and anchor itself to the vessel 20. As illustrated in FIG. 3C, the deployment of tubular insertion device 22 and expansion of the barbed suture 10 allows for the capture of circulating platelets and blood components to instigate vascular blockage and/or clotting of vessel 20.

The barbed suture in FIGS. 3A-3C illustrates a flexible and bent configuration. However, it is envisioned that a variety of suture or fiber configurations may be employed. In other embodiments, fiber configurations may include twisting the barbed device within the sheath (not shown).

In an exemplary embodiment, where present, a tubular insertion device surrounding a barbed suture of the present disclosure protects the bioactive agent which is disposed within the barb angle formed by the barb and the suture body. Thus, the tubular insertion device may aid in keeping the barbed suture intact and the bioactive agent attached to the surface of the suture during insertion, as well as during handling, and storage of the suture. This minimizes the loss of bioactive agent to the packaging of the medical device, the environment, etc. However, upon engaging the barbed suture and tubular insertion device in vivo, moving the sheath relative to the suture to extract the sheath from the tissue exposes the bioactive agent to tissue and assists in the release of bioactive agent from the interface of the barb and the suture body into the wound closure. The barbed suture expands to full vessel thickness and acts as an anchor to patient tissue.

In embodiments where a clotting agent is employed, the barbed suture also captures circulating platelets and blood components and instigates vascular blockage or clotting. If mechanical property requirements are not too restrictive, a hydrogel or super-absorbent material may be used to further concentrate blood components, or the barbed device may also drive and place the hydrogel-like material to final placement.

Figure 4A:
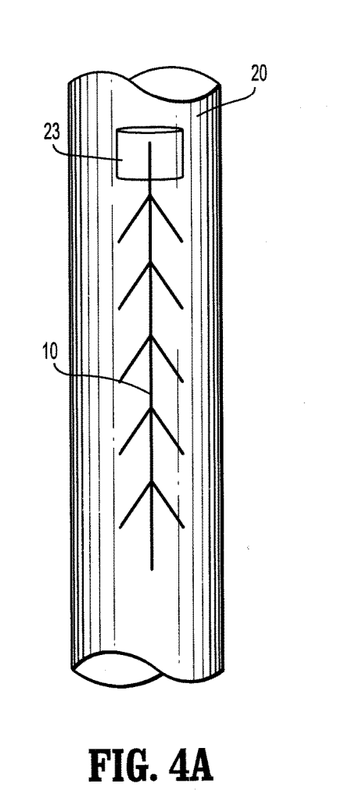
FIGS. 4A-4B are plan views of a sheath utilized with a barbed suture.
Figure 4B:
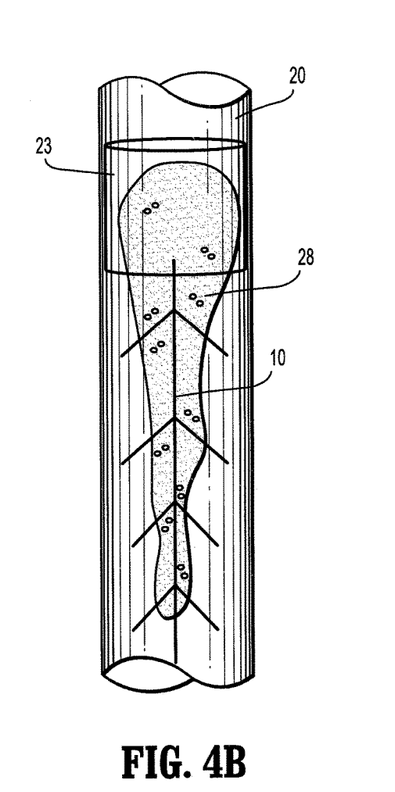

Referring to FIGS. 4A-4B, a sheath 23 may be utilized to introduce barbed suture 10 in accordance with the present disclosure into blood vessel 20. Such a sheath 23 may have a tubular body in which the barbed suture 10 is disposed. In one embodiment, sheath 23 may be disposed at one end of barbed suture 10 and in other embodiments, sheath 23 may be disposed on both ends of barbed suture 10 (not shown). In embodiments, sheath 23 may be formed of materials such as, but are not limited to, filament fibers, nylon fibers, polyester (PET), copolymer polyester (co-PET), polypropylene (PP), and polyethylene (PE). [please confirm] which are designed to swell in order to block vessel 20 and induce clotting as the barbs on the suture, fully engaged and expanded within vessel 20, captures blood components and platelets to assist in the clotting. The barbed suture 10 may also include a bioactive agent within the included angle of the barb and the elongated body of the suture to enhance clotting of vessel 20.

Methods for repairing tissue with the sutures of the present disclosure are also provided. The sutures of the present disclosure may be utilized in any cosmetic endoscopic or laparoscopic methods. In addition, sutures of the present disclosure may be utilized to attach one tissue to another including, but not limited to, attaching tissue to a ligament.

In embodiments, sutures of the present disclosure may be held in place without the need for knots. In such cases, tissue located over a suture of the present disclosure placed in vivo may be physically manipulated or massaged into a desired position to enhance the holding of tissue in the desired position. In embodiments, the physical manipulation of tissue located over a suture of the present disclosure may enhance the release of any medicinal agent located on the suture, including any medicinal agent found in the angle between a barb and the body of a suture of the present disclosure.

For example, sutures of the present disclosure may be utilized to provide lift to tissue, which may be desirable in certain cosmetic applications. In embodiments, a procedure for closing tissue utilizing sutures includes inserting a first end of a suture, optionally attached to a needle, at an insertion point on the surface of a person's body. The first end of the suture may be pushed through soft tissue until the first end extends out of the soft tissue at an exit point. The first end of the suture may then be gripped and pulled to draw the first portion of the suture through the soft tissue so that a length of the first portion of the suture remains in the soft tissue between the point of insertion and exit point of the first end. The soft tissue may then be manually grouped and advanced along at least one portion of the suture to provide the desired amount of lift.

Specific applications of cosmetic surgeries which may utilized this physical manipulation of a suture as described above include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities, including the use of other wound closure devices, within the scope and spirit of the disclosure as defined by the claims appended hereto.

What is claimed is:

1. A surgical suture comprising:
   an elongated body including barbs projecting at an angle from the elongated body; and
   a bioactive agent deposited solely within the angle between the barbs and the elongated body, the amount of the bioactive agent being from about 0.01% by weight to about 2% by weight of the suture.

2. The surgical suture of claim 1, wherein the barbs are aligned in a same direction along the elongated body.

3. The surgical suture of claim 1, wherein the barbs on a first portion of the elongated body are aligned in a first direction and the barbs on a second portion of the elongated body are aligned in a second direction.

4. The surgical suture of claim 1, wherein the bioactive agent is selected from the group consisting of biocidal agents, antimicrobial agents, medicaments, growth factors, anti-clotting agents, clotting agents, analgesics, anesthetics, anti-inflammatory agents, wound repair agents, chemotherapeutics, biologics, protein therapeutics, antibodies, DNA, RNA, peptides, polysaccharides, lectins, lipids, anti-angiogenic drugs, polymeric drugs, and combinations thereof.

5. The surgical suture of claim 4, wherein the antimicrobial agent is selected from the group consisting of antibiotics, antiseptics, disinfectants, and combinations thereof.

6. The surgical suture of claim 5, wherein the antimicrobial agent is an antiseptic selected from the group consisting of hexachlorophene, chlorhexidine, cyclohexidine, iodine, povidone-iodine, p-chloro-m-xylenol, triclosan, nitrofurantoin, nitrofurazone, methenamine, glutaraldehyde, formaldehyde, alcohols, and combinations thereof.

7. The surgical suture of claim 4, wherein the antimicrobial agent is selected from the group consisting of anthracycline, doxorubicin, mitoxantrone, a fluoropyrimidine, 5-fluorouracil, a folic acid antagonist, methotrexate, podophylotoxin, etoposide, camptothecin, hydroxyurea, a platinum complex, cisplatin, doxycycline, metronidazole, trimethoprim-sulfamethoxazole, rifamycins, rifampin, polyvinyl pyrrolidone, fourth generation penicillins and analogues and derivatives thereof, a first generation cephalosporins and analogues and derivatives thereof, a second generation cephalosporin and analogues and derivatives thereof, a third generation cephalosporin and analogues and derivatives thereof, a fourth generation cephalosporin and analogues and derivatives thereof, a monobactam, a carbapenem, an aminoglycoside, a macrolide, a lincosamide, a streptogramin, erythromycin, azithromycin, clindamycin, syneroid, clarithromycin, kanamycin sulfate, tetracyclines, fusidic acid, trimethoprim, metronidazole, a quinolone, a DNA synthesis inhibitor, a sulfonamide, beta-lactam inhibitors, chloramphenicol, glycopeptides, mupirocin, polyenes, azoles, and combinations thereof.

8. The surgical suture of claim 4, wherein the chemotherapeutic is selected from the group consisting of doxorubicin, paclitaxel, camptothecin, polyglutamate-PTX, N-(2-hydroxypropyl)methacrylamide copolymer, anthracycline, letrozole, anastrozole, epidermal growth factor receptor inhibitors, tyrosine kinase inhibitors, modulators of apoptosis, anthracycline antibiotics, daunorubicin, doxorubicin, alkylating agents, cyclophosphamide, melphalan, antimetabolites, methotrexate, 5-fluorouracil, poly(ethylene glycol), poly(glutamic acid), polysaccharides, polymer-drug conjugates thereof, copolymers thereof, and combinations thereof.

9. The surgical suture of claim 4, wherein the clotting agent is selected from the group consisting of human growth factors, magainin, plasminogen activator, superoxide dismutase, tumor necrosis factor, colony stimulating factor, interferon, interleukin-2, lymphokines, fibrin, chitosin, silk, talc, polylysine, fibronectin, bleomycin and analogues and derivatives thereof, collagen, metallic beryllium and oxides thereof, copper, saracin, silica, crystalline silicates, quartz dust, talcum powder, ethanol, extracellular matrix, fibrinogen, poly(ethylene terephthalate), poly(ethylene-co-vinylacetate), cyanoacrylate, cytokines, dexamethasone, isotretinoin, estradiols, diethylstibesterol, cyclosporine a, all-trans retinoic acid and analogues and derivatives thereof, wool, cotton, polyurethane, polytetrafluoroethylene, poly (alkylcyanoacrylate), activin, angiopoietin, colony-stimulating factor, erythropoietin, endothelin-1, angiotensin II, bromocriptine, methylsergide, fibrosin, glycoproteins, proteoglycan, hyaluronan, secreted protein acidic and rich in cysteine, a thrombospondin, tenacin, a cell adhesion molecule, an inhibitor of matrix metalloproteinase, methotrexate, carbon tetrachloride, thioacetamide, superoxide dismutase, tumor necrosis factor, colony stimulating factor, platelet rich plasma, thrombin, and combinations thereof.

10. The surgical suture of claim 4, wherein the polymer drug is selected from the group consisting of steroidal anti-inflammatory agents, non-steroidal anti-inflammatory agents, and combinations thereof.

11. The surgical suture of claim 10, wherein the non-steroidal anti-inflammatory agent is selected from the group consisting of aspirin, indomethacin, ibuprofen, phenylbutazone, diflusinal, and combinations thereof.

12. The surgical suture of claim 10, wherein the steroidal anti-inflammatory agent is selected from the group consisting of glucocorticoids, cortisone, hydrocortisone, betamethasone, dexamethasone, fluprednisolone, prednisone, methylprednisolone, prednisolone, triamcinolone, paramethasone, and combinations thereof.

13. The surgical suture of claim 1, wherein the elongate body is made from a material selected from the group consisting of degradable materials, non-degradable materials, and combinations thereof.

14. The surgical suture of claim 1, wherein the elongate body comprises a degradable material selected from the group consisting of trimethylene carbonate, tetramethylene carbonate, caprolactone, valerolactone, dioxanone, glycolic acid, lactic acid, glycolide, polyanhydrides, polyesters, polyacrylates, polymethylmethacrylates, polyurethanes, polyorthoester, polyhydroxy alkanoates, polyhydroxy butyrate, lactide, homopolymers thereof, copolymers thereof, and combinations thereof.

15. The surgical suture of claim 1, wherein the elongate body comprises a non-degradable material selected from the group consisting of polyethylene, polypropylene, copolymers of polyethylene and polypropylene, blends of polyethylene and polypropylene, polyethylene terephthalate, polytetrafluoroethylene, polybutester, polytetramethylene ether glycol, 1,4-butanediol, silk, collagen, ultrahigh molecular weight polyethylene, and combinations thereof.

16. The surgical suture of claim 1, further comprising a coating on at least a portion of the suture.

17. The surgical suture of claim 16, wherein the coating comprises a degradable polymer.

18. The surgical suture of claim 16, wherein the coating is selected from the group consisting of trimethylene carbonate, tetramethylene carbonate, caprolactone, valerolactone, dioxanone, glycolic acid, lactic acid, glycolide, polyanhydrides, polyesters, polyacrylates, polymethylmethacrylates, polyurethanes, polyorthoester, polyhydroxy alkanoates, polyhydroxy butyrate, lactide, polymer drugs, homopolymers thereof, copolymers thereof, and combinations thereof.

19. The surgical suture of claim 16, wherein the coating further comprises at least one monomer selected from the group consisting of alkylene carbonates, dioxanones, dioxepanones, degradable cyclic amides, degradable cyclic ether-esters derived from crown ethers, alpha hydroxyacids, beta hydroxyacids, polyalkyl ethers, polyvinyl pyrrolidone, hydroxyethylmethacrylate, phosphorylcholine, acrylic acid, methacrylic acid, vinyl monomers, vinyl alcohols, vinyl acetate, and combinations thereof.

20. The surgical suture of claim 16, wherein the coating further comprises one or more fatty acid components selected from the group consisting of fatty acids, fatty acid salts, and salts of fatty acid esters.

21. The surgical suture of claim 1, wherein the angle between the barbs and the suture body is less than 90 degrees.

22. The surgical suture of claim 1, wherein the barbs are integrally formed with the elongated body.

23. A method comprising closing a wound with a suture of claim 1.

24. The method of claim 23, wherein the suture is affixed to a needle.

* * * * *